United States Patent

Pilo et al.

[11] Patent Number: 5,665,099
[45] Date of Patent: Sep. 9, 1997

[54] SURGICAL SCALPEL WITH AUTOMATICALLY RETRACTABLE BLADE

[76] Inventors: Giuseppe Pilo, via Muroni 22; Antonio Giovanni Flumene, via Garavetti 6, both of 07100 Sassari, Italy

[21] Appl. No.: 440,419

[22] Filed: May 12, 1995

[51] Int. Cl.⁶ ................................. A61B 17/32
[52] U.S. Cl. ......................... 606/167; 30/162
[58] Field of Search ............... 30/162, 335, 336; 606/167, 170

[56] References Cited

U.S. PATENT DOCUMENTS

| | | | |
|---|---|---|---|
| 2,619,724 | 12/1952 | Manthey et al. | 30/336 |
| 3,590,808 | 7/1971 | Muller | 128/752 |
| 3,977,079 | 8/1976 | Rebold | 30/336 |
| 5,211,652 | 5/1993 | Derbyshire | 606/182 |

FOREIGN PATENT DOCUMENTS 1284979  8/1972  United Kingdom .............. 30/323

*Primary Examiner*—Michael Buiz
*Assistant Examiner*—Patrick W. Rasche

[57] ABSTRACT

A surgical scalpel includes a blade carried by a blade support, which is slidable within an outer sheath. The blade support is movable from a first position in which the blade is within the sheath to a second position in which the blade is exposed. One end of the blade support has a hollow cylinder, in which a stationary piston is disposed. Movement of the blade support from the first position to the second position creates a vacuum within the hollow cylinder, so that when the surgeon releases his or her grip on the scalpel, the blade support is quickly and automatically retracted to the first position.

17 Claims, 4 Drawing Sheets

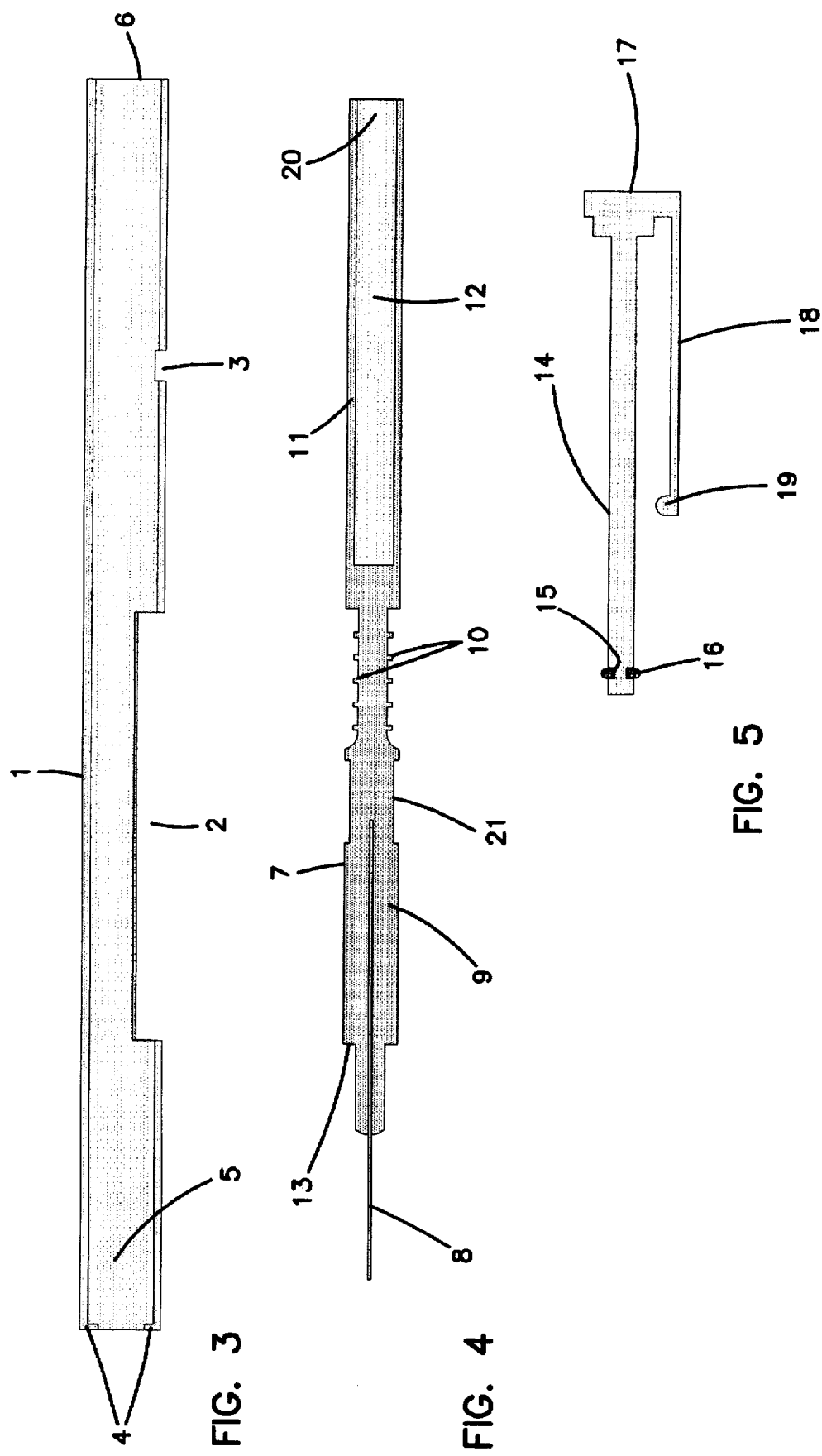

SURGICAL SCALPEL WITH AUTOMATICALLY RETRACTABLE BLADE

BACKGROUND OF THE INVENTION

The present invention is directed to a safety surgical scalpel for medical use, having an automatically retractable blade. The present invention can be applied both to disposable scalpels and reusable scalpels.

Many scalpels presently on the market, both of the single-use and the reusable type, are provided with an exposed fixed or interchangeable blade. The exposed blade of such devices exposes the surgeon and those in the operating theater to the risk of serious diseases, such as HIV or vital hepatitis, since the hand-to-hand passing of the bare blade, often contaminated with the blood of the patient, during surgical procedures can cause accidental injury.

To reduce this risk, several blade protection systems have been proposed. For example, WO-90-11725 describes a surgical scalpel which includes a complex mechanism for moving the sheath relative to the blade, to expose the blade in operation. The complexity of this scalpel renders it unsuitable for disposable applications, as well as resulting in a complex manufacturing process. Similarly, EP217638 describes a highly-specialized and complex instrument. However, even in this instrument, the blade must be changed before use, which in itself creates a dangerous situation. PCT/EP93/01458 describes a disposable scalpel provided with a relatively simple mechanical system for retracting the blade. While this scalpel has some advantages, it still has not been completely successful in terms of the ease of its use, so that further improvement has been desired. Retractable blades have also been considered in the context of hand tools such as utility knives (see U.S. Pat. No. 4,028,758, DE-A-3725294 and B-8801175). Such hand tools bear little relationship to the problems faced in designing a surgical scalpel suitable for use in the operating theater.

SUMMARY OF THE INVENTION

It is an object of the present invention to provide a surgical scalpel having a blade which is automatically retractable, which can be operated by the hand holding the scalpel to move the blade between a protected and an exposed position, where the blade is automatically retracted when the surgeon's finger is removed.

It is a further object of the present invention to provide such a scalpel in which the finger pressure required to maintain the blade in the exposed position is similar to the finger pressure required to hold the scalpel while in use.

It is a still further object of the present invention to provide a scalpel which fits comfortably within the hand of the surgeon, is capable of precise manipulation and does not obstruct the surgeon's view of the blade while in use.

It is a still further object of the present invention to provide a scalpel with an automatically retractable blade which can be used by right-handed and left-handed surgeons.

It is a still further object of the present invention to provide a scalpel with an automatically retractable blade which can be used by holding the posterior extremity of the scalpel to maintain the blade in an exposed position, so as to permit use of the scalpel in deep surgical fields.

It is a still further object of the present invention to provide a scalpel with an automatically retractable blade which is of simple and inexpensive construction.

BRIEF DESCRIPTION OF THE DRAWINGS

The foregoing and other objects, features and advantages of the present invention will be understood more completely from the following detailed description of the present invention, with reference being had to the accompanying drawings, in which:

FIGS. 3, 4 and 5 are sectional views showing the sheath, blade holder and piston of the scalpel of the present invention.

DETAILED DESCRIPTION OF THE PREFERRED EMBODIMENT

Referring to FIGS. 1, 3, 4 and 5, the scalpel of the present invention includes three main components, namely sheath 1, blade holder 7 and piston 14.

Figure 6:
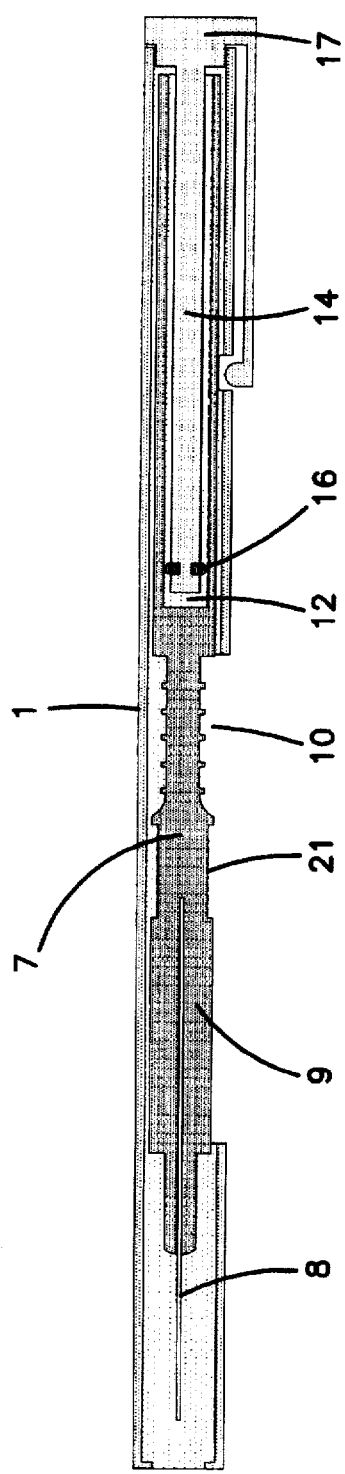
FIGS. 6, 7 and 8 are sectional views of the scalpel of the present invention, showing the scalpel with the blade in the protected position, an exposed position, and an exposed position for operating on a deep surgical field, respectively.
Figure 7:
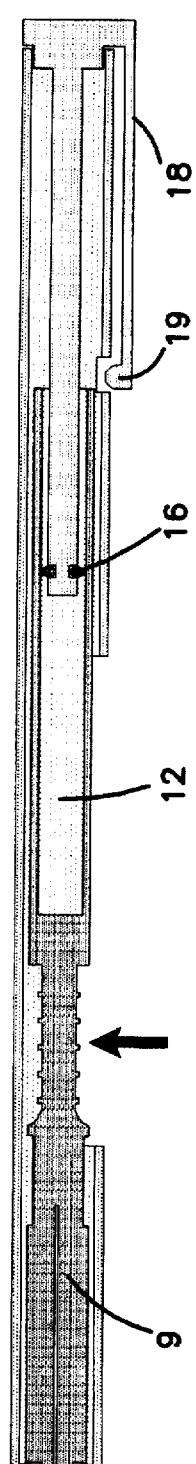
Figure 8:
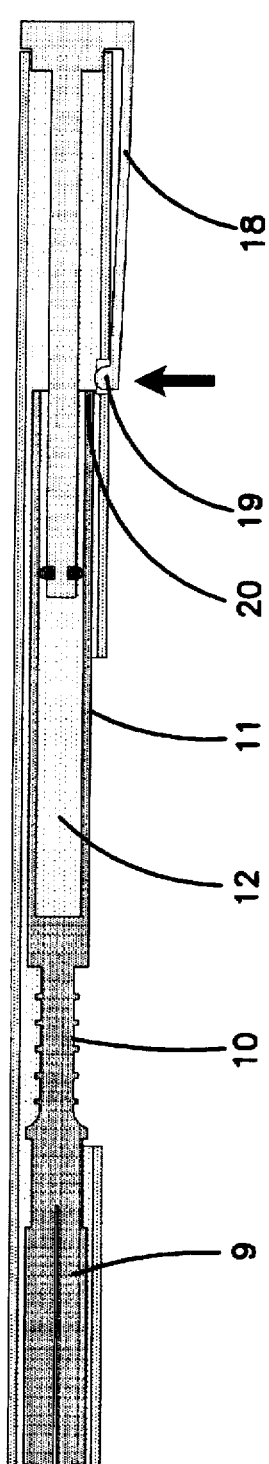

Referring to these figures and further to FIGS. 6–8, it can be seen that the sheath 1 is a hollow, elongated cylinder having ends 5 and 6. The scalpel blade 8 extends through open end 5 of the sheath in use. The side wall of the sheath is interrupted by lateral windows 2 and 3. These permit access to the interior of the sheath.

Blade support 7 is also in the form of an elongated cylinder. The blade support 7 has a first end 9 which grips the scalpel blade 8. The second end 11 of the blade holder 7 can be hollow to define a vacuum chamber 12 in a manner discussed below. The blade support 7 is provided with a gripping surface 10, which can be defined by two opposed flattened portions on a side of the blade support. It is preferable that the portions 10 are accessible through opening 2, especially when the blade support is in the position where the blade is exposed. It is preferable to provide the portions 10 with gripping aids, which can be in the form of a plurality of ribs extending in the direction perpendicular to the longitudinal direction of the blade support.

The second end 6 of the sheath is closed by cap end 17 on piston 14. Piston 14 is disposed in vacuum chamber 12, with hollow end 11, and thus blade support 7, being allowed to move forward, to expose the blade, and backward, to retract the blade. A groove 15 is provided at the internal end of the piston, for carrying O-ring 16. The O-ring 16 permits sliding movement of the blade support, while maintaining a substantially air-tight seal. That is, the seal is sufficient to permit the development of a vacuum in chamber 12 when the blade is exposed which will retract the blade support upon release of gripping pressure on the blade support. The cap end 17 can be provided with an arm 18 which extends longitudinally in the direction of the first end of the sheath 5, and which is in turn provided with a detent 19 which is able to extend through second opening 3 on the sheath, to maintain the blade support and the blade in the exposed position, for use in deep surgical fields.

The vacuum system is generated by inserting the piston 14 with the O-ring into the chamber 12, and at the same time pushing out the air present in the chamber. This can be accomplished by interrupting the seal between the O-ring and the wall of the chamber 12 with a small diameter synthetic thread (for example, monofilament fishing line) between the O-ring and the wall of chamber 12 when the piston is inserted into the chamber. When the piston has been fully inserted into the chamber 12, the fishing line can be removed to permit the full establishment of the seal.

Figure 1A:
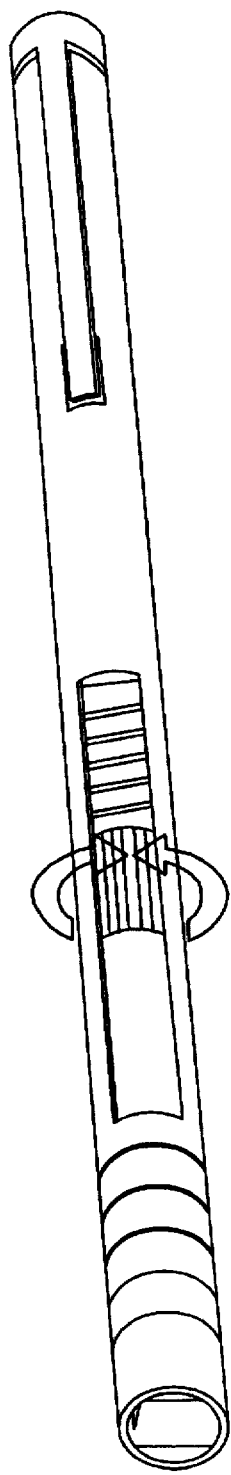
FIG. 1 illustrates perspective views of the scalpel of the present invention with the blade in a protected position and in an exposed position.
Figure 1B:
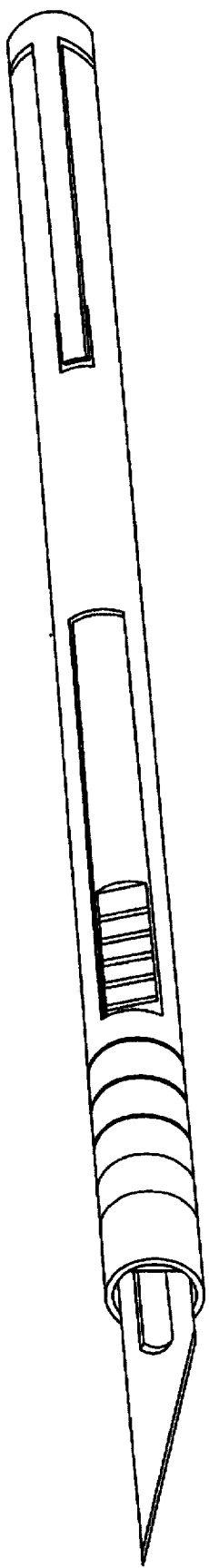
Figure 2A:
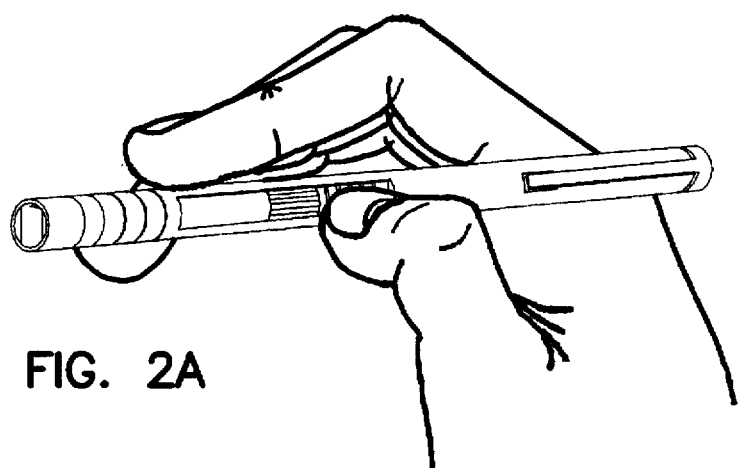
FIGS. 2A–C illustrate perspective views of the scalpel of the present invention being grasped by a surgeon's hand, with FIG. 2A showing the scalpel with the blade in the protected position, FIG. 2B showing the scalpel with the blade in the exposed position and FIG. 2C showing the scalpel with the blade in the exposed position, but being grasped for use in a deep surgical field.
Figure 2B:
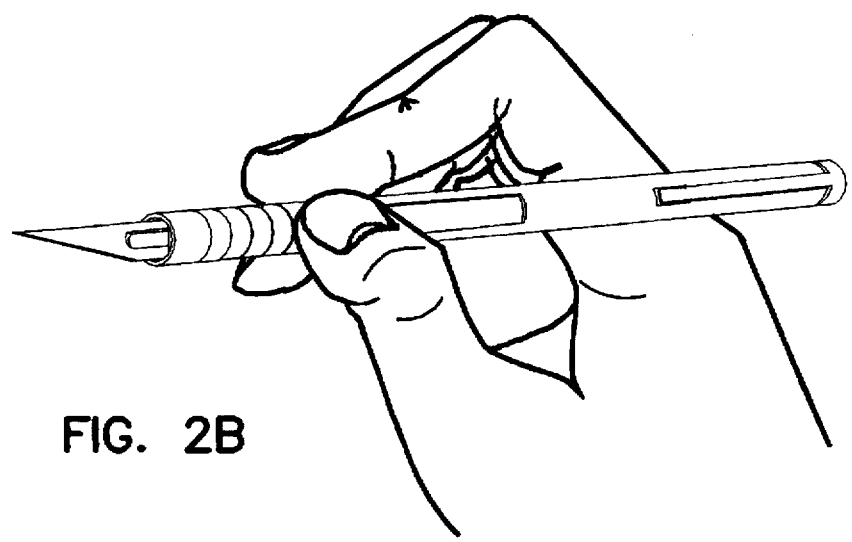
Figure 2C:
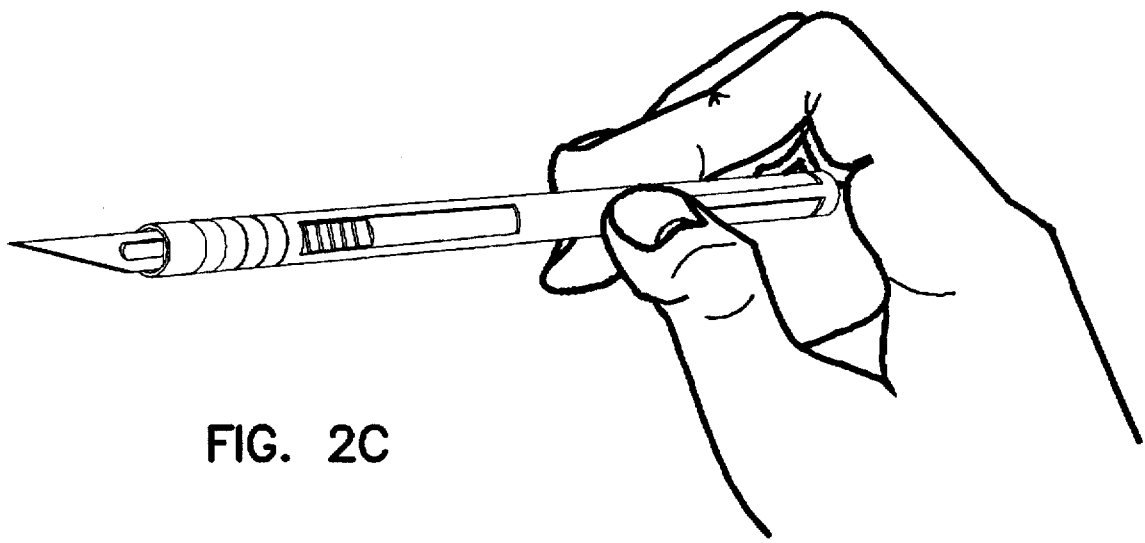

The use of the present scalpel will now be described, with reference to FIGS. 2A–C and FIGS. 6–8. As can be seen in FIGS. 2A and 6, the blade holder is initially in a position with the blade protected. To use the scalpel, the surgeon uses his finger or thumb to slide the blade holder 7 in the direction of the open end 5 of the sheath. This puts blade 8 in an exposed position. It is preferable for the exposed position for the blade to be defined by the engagement of inwardly-extending lip 4 at the open end 5 of the sheath (see FIG. 3) with end surface 13 of the blade support 7 (see FIG. 4).

Since O-ring 16 forms a substantially air-tight seal with the wall of the chamber 12, the movement of the blade support 7, which causes relative movement between the chamber wall and the fixed piston 14 and greatly expands the effective volume of chamber 12, creates a vacuum in chamber 12. When the surgeon is done with the scalpel and releases the pressure of his finger or thumb, the vacuum created in chamber 12 automatically will return blade support 7 to the original position, i.e. with the blade in the protected position.

To permit use of the scalpel in a deep surgical field, arm 18 is positioned so that detent 19 can extend through the second opening 3 in the side wall of the sheath. Thus, with the blade in the exposed position, pressure on arm 18 urges detent 19 to extend through the opening 3 to provide a stop which engages the end 20 of the blade support, preventing the retraction of the blade from the exposed position. Again, when the surgeon releases the clip (i.e., arm 18), the vacuum in chamber 12 retracts the blade support so that the blade is again in the protected position. It will, of course, be understood that the surgeon will be required to use his other hand to hold the blade in the exposed position through opening 2 while detent 19 is moved into position.

It also is preferred that the blade support 7 be rotatable about its longitudinal axis within the sheath 1. This permits the same scalpel to be used by left-handed or right-handed surgeons. To change between the two, it is necessary only to rotate the blade support through 180° of rotation. Longitudinally-extending ribs 21 can be provided to aid this operation. The provision of the two opposed flattened portions 10 provides the same gripping surface for both right- and left-handed use.

It should be noted that the configuration of lip 4 can be changed to fit various needs also. For example, in one case it may be desirable to configure lip 4 and blade support 7 so that rotation of the blade support is prevented when the blade is in the exposed position. In other cases, for example, when the blade is small or in microsurgery use, the lip can be circular in nature, since in these cases some rotation of the blade is sometimes required during use.

By way of example, the sheath may have a length of about 15 cm and a diameter of about 1 cm. Cylinder 11 may have a length of about 5 cm. The opening 2 may have a length of about 4.5 cm, and may start at a point about 3 cm from the first end 5 of the sheath. The second opening 3 may be located about 3 cm from the end 6 of the sheath.

The present invention is applicable both to disposable scalpels and reusable scalpels (e.g. a diamond-blade scalpel). In the case of the disposable scalpel, the sheath, blade holder and piston can be made of plastic materials. For example, clear 7 polycarbonate can be used for the sheath and polypropylene or polyvinylchloride (PVC) for the blade support and piston, such as a colored polymeric material known by the name MOPLEN. The O-ring can be made of rubber or silicone. In the case of the reusable scalpel, of course the parts of the scalpel usually will be made of stainless steel, except for the O-ring, which again can be made of rubber or silicone.

In addition, while the illustrated embodiment is provided with a fixed piston 14 secured to the second end 6 of the sheath and a hollow-ended blade support 7, it also would be possible to mount cylinder 11 on the end of the sheath and provide the piston 14 on the second end of blade support 7.

Although a detailed description of the present invention has been provided above, those skilled in the art will understand that variations may be made without departing from the principles disclosed herein. Thus, the present invention is not limited to the disclosed embodiments, but rather is defined by the appended claims.

What is claimed is:

1. An automatically retracting scalpel, comprising:

a sheath having a sidewall, an open first end and a second end;

a blade support having a first end carrying a scalpel blade and a second end, said blade support being slidably disposed in the sheath and capable of movement from a first position in which the scalpel blade is within the sheath and a second position in which the blade extends beyond the first end of the sheath;

a cylinder; and a piston slidably moveable with respect to the cylinder and substantially air-tightly sealed to the cylinder, one of the piston and the cylinder being disposed at the second end of the blade support, the other of the piston and the cylinder being disposed at the second end of the sheath, whereby movement of the blade support from the first position to the second position causes relative movement between the piston and the cylinder to create a vacuum in the cylinder capable of retracting the blade support to the first position, and wherein the sidewall of the sheath is provided with a first opening permitting access to the blade support to allow a user's digit to hold the blade support in the second position.

2. The scalpel of claim 1, further comprising an O-ring carried by the piston.

3. The scalpel of claim 1, wherein the first end of the sheath is provided with an inwardly-extending lip and the first end of the blade support comprises a surface for engaging the lip when the blade support reaches the second position.

4. The scalpel of claim 1, wherein the blade support, in the first position, is rotatable within the sheath.

5. The scalpel of claim 4, wherein the blade support further comprises longitudinal ribs, which are accessible through the first opening when the blade support is in the first position.

6. The scalpel of claim 1, wherein the blade support further comprises a gripping surface which is accessible through the first opening when the blade support is in the second position.

7. The scalpel of claim 6, wherein the sheath and the blade support are substantially cylindrical in nature, the gripping surface being formed of a flattened portion of a side of the blade support.

8. The scalpel of claim 7, wherein the gripping surface comprises ribs which extend substantially perpendicular to the longitudinal direction of the blade support.

9. The scalpel of claim 8, wherein the gripping surface is accessible through the first opening when the blade support is in the first position.

10. An automatically retracting scalpel, comprising:

a sheath having an open first end and a second end;

a blade support having a first end carrying a scalpel blade and a second end, said blade support being slidably disposed in the sheath, and capable of movement from a first position in which the scalpel blade is within the sheath to a second position in which the blade extends beyond the first end of the sheath;

a cylinder fixed to the second end of the blade support; and a piston fixed to the second end of the sheath, the piston being slidably moveable with respect to the cylinder and substantially air-tightly sealed to the cylinder, whereby movement of the blade support from the first position to the second position causes relative movement between the piston and the cylinder to create a vacuum in the cylinder capable of retracting the blade support to the first position.

11. The scalpel of claim 10, wherein the sheath has a sidewall which is provided with a first opening permitting access to the blade support to allow a user to maintain the blade support in the second position.

12. The scalpel of claim 11, wherein the sheath and the blade support are substantially cylindrical in nature, the blade support further comprising a gripping surface which is accessible through the first opening when the blade support is in the second position, the gripping surface being formed of opposed flattened portions on a side of the blade support, the blade support being rotatable within the sheath when in the first position to permit one or the other of the flattened portions to be accessible through the first opening.

13. The scalpel of claim 12, wherein the gripping surface is accessible through the first opening when the blade support is in the first position.

14. The scalpel of claim 12, wherein the blade support further comprises longitudinal ribs, which are accessible through the first opening when the blade support is in the first position.

15. The scalpel of claim 11, wherein the sidewall of the sheath is provided with a second opening in the area of the second end, permitting access to the interior of the sheath to allow a user to hold the scalpel at the second end of the sheath and maintain the blade support in the second position.

16. The scalpel of claim 15, wherein the second end of the sheath is closed with a cap which comprises an arm extending longitudinally in the direction of the first end of the sheath, the arm comprising a detent which, when pressure is applied to the arm, is capable of extending through the second opening to maintain the blade support in the second position.

17. The scalpel of claim 16, wherein when the blade support is in the second position, the second end of the blade support is on the first end side of the second opening, whereby the detent can engage the second end of the blade support to maintain the blade support in the second position.

* * * * *